United States Patent [19]

Bodenmuller et al.

[11] Patent Number: 5,580,742

[45] Date of Patent: Dec. 3, 1996

[54] METHOD FOR THE DETECTION OF PROTEINS CONTAINING PHOSPHORYLATED TYROSINE

[75] Inventors: Heinz Bodenmuller; Andreas Dessauer, both of Tutzing, Germany

[73] Assignee: Boehringer Mannheim GmbH, Mannheim, Germany

[21] Appl. No.: 183,898

[22] Filed: Jan. 21, 1994

Related U.S. Application Data

[63] Continuation of Ser. No. 919,396, Jul. 29, 1992, abandoned, which is a continuation of Ser. No. 672,292, Mar. 20, 1991, abandoned.

[30] Foreign Application Priority Data

Mar. 27, 1990 [DE] Germany .......................... 40 09 848.6

[51] Int. Cl.$^6$ ...................... G01N 33/547; G01N 33/567; G01N 33/577
[52] U.S. Cl. .......................... 435/7.94; 435/7.5; 436/520; 436/532; 436/822
[58] Field of Search .................................... 435/7.94, 7.5, 435/975; 436/545, 533, 520, 544, 546, 532

[56] References Cited

U.S. PATENT DOCUMENTS

| | | | |
|---|---|---|---|
| 4,543,439 | 9/1985 | Frackelton, Jr. | 935/92 |
| 4,758,522 | 7/1988 | O'Connor | 436/501 |

FOREIGN PATENT DOCUMENTS

| | | |
|---|---|---|
| 314388 | 5/1989 | European Pat. Off. . |
| 0322768 | 7/1989 | European Pat. Off. . |
| 0322813 | 7/1989 | European Pat. Off. . |
| 0353895 | 2/1990 | European Pat. Off. . |
| 0356964A3 | 3/1990 | European Pat. Off. . |

OTHER PUBLICATIONS

*Chemical Abstracts*, vol. 112, No. 1, Jan. 1, 1990, Kharitonenkov et al, "Preparation of monoclonal antibodies to phosphotyrosine and their use for identification of phosphotyrosin–containing proteins.".

*Nature*, vol. 294, No. 5842, Dec. 17, 1981, Ross et al, "Phosphotyrosin–containing proteins isolated by affinity chromatography with antibodies to a synthetic hapten", pp. 654–656.

K. H. Lau et al., Biochem. J. (1989) 257, 23–36. Phosphotyrosyl protein phosphatases.

M. Torosian, Surgery, Gynecology and Obstetrics, vol. 166 (1988) 567–579. The clinical usefulness and limitations of tumor markers.

Y. Durocher et al., Cancer Research, 49, 4818–4823 (1989). Tyrosine Protein Kinase Activity of Human Hyperplastic Prostate and Carcinoma Cell Lines PC3 and DU145.

Documenta Geigy, Wissenschaftl. Tabellen, 7th edition (1975), 592, Verlag, Stuttgart.

Rudinger et al., Derwent Abstract of European patent 322, 813 published Jul. 1989.

J. Wang, Analytical Biochemistry, vol. 172, pp. 1–7 (1988).

*Primary Examiner*—Mary E. Ceperley
*Attorney, Agent, or Firm*—Nikaido, Marmelstein, Murray & Oram, LLP

[57] ABSTRACT

For the detection of proteins containing phosphorylated tyrosine the sample of a body fluid is incubated with at least two receptors $R_1$ and $R_2$ whereby a change in signal is produced by binding of at least the receptors $R_1$ and $R_2$ with the substance to be detected in the sample solution and in which in each case one of the two receptors contains an antibody or its derivative capable of specifically binding to the protein to be detected and the other receptor contains an antibody or its derivative capable of specifically binding to phosphorylated tyrosine and the signal change caused by the binding is determined in the sample.

8 Claims, No Drawings

METHOD FOR THE DETECTION OF PROTEINS CONTAINING PHOSPHORYLATED TYROSINE

DESCRIPTION

This application is a continuation of application Ser. No. 07/919,396, filed on Jul. 29, 1992, now abandoned which is a continuation of Ser. No. 07/672,292, filed on Mar. 20, 1991, now abandoned.

The invention concerns a method for the detection of proteins containing phosphorylated tyrosine and a combination of reagents which is suitable therefor.

One of the most important modifications of proteins is their phosphorylation. In this process phosphorus groups are transferred by the action of protein kinases to a suitable site on the protein. The amino acids containing hydroxyl groups, and in fact mainly serine or threonine, are often phosphorylated thereby. In normal cells a great preference is given to the phosphorylation of serine and threonine compared to the phosphorylation of tyrosine whereby more than 99% of the phosphate groups are present on serine and threonine.

An increased occurrence of phosphotyrosine kinase activity has now been established in transformed cells. As a result the proportion of phosphotyrosine in transformed cells can increase by a factor of 5 to 70. The occurrence of proteins containing phosphotyrosine is therefore associated with the transformation of cells. It is also being discussed to what extent the degree of phosphorylation can indicate the malignity of a cell.

In addition, it was observed that many oncogene proteins have a tyrosine kinase activity i.e. they can phosphorylate themselves and also other proteins at the tyrosine positions. Such oncogene proteins occur in the plasma membrane as well as in the cytoplasm. Since then, as a rule, oncogenes represent factors which have the same function as proto-oncogenes in normal cells but have a changed regulation or even none at all, the corresponding products can occur in increasing amounts in the cells. It has already been attempted to detect products of these enzyme activities. Experiments with radioactive phosphorus $^{32}p$ were carried out for this which, however, are only possible in cell cultures and which make investigations in animals or even humans impossible.

It has also already been proposed that proteins containing phosphorylated tyrosine be detected by immunological means. The methods known up to now have, however, failed because they also detected proteins by cross-reactions which did not contain any phosphorylated tyrosine.

It was therefore the object of the present invention to provide a method by which proteins in body fluids which are phosphorylated at the tyrosine can be determined in terms of type and amount in a simple and rapid manner.

This object is achieved by a method for the detection of proteins containing phosphorylated tyrosine, which is characterized in that the sample of a body fluid is incubated with at least two receptors $R_1$ and $R_2$ whereby a change in signal is produced by binding of at least the receptors $R_1$ and $R_2$ with the substance to be detected in the sample solution and in which in each case one of the two receptors contains an antibody or its derivative capable of specifically binding to the protein to be detected and the other receptor contains an antibody or its derivative capable of specifically binding to phosphorylated tyrosine and the signal change caused by the binding is determined in the sample.

It is possible with the method according to the present invention to detect proteins containing phosphorylated tyrosine in body fluids exactly and reproducibly. The degree of phosphorylation and the type of the phosphorylated protein can be determined rapidly and simply by the combination of two different antibodies.

The method of detection is carried out in body fluids, preferably serum. Very many variants are known for carrying out the intended immunological method of determination according to the invention which are all suitable in this case. Thus, two or three, or even more, receptors can be used and the incubation with the individual receptors can take place in various orders in a homogeneous or heterogeneous phase. These variants of the method are known to one skilled in the art and therefore do not need to be elucidated here in more detail.

In each case a change in signal resulting from the binding of at least two receptors with the substance to be detected in the sample solution is evaluated. Depending on the system used this change in signal can be e.g. colour change, change in turbidity or change in fluorescence. In each case at least two receptors are used whereby the change in signal only takes place if $R_1$ as well as $R_2$ are bound to the substance to be deteced. The test can be carried out with homogeneous methods such as e.g. the agglutination assay in which coated particles such as e.g. latex particles or erythrocytes are used as receptors which become cross-linked by binding to the substance to be detected and thereby agglutinate or with heterogeneous methods such as for example a sandwich immunoassay.

In each case two receptors are used of which one contains an antibody or its derivative capable of specifically binding to the protein to be detected and the other contains an antibody or its derivative capable of binding to phosphorylated tyrosine.

The antibody used for the receptor $R_1$ is preferably an antibody or its derivative directed against the protein to be detected. Proteins which are detected according to the present invention are those which often occur in tumour tissues and which are substrates for phosphotyrosine kinases. Examples are: receptors of proteohormones with autocatalytic phosphorylation such as epideral derived growth factor-R., platelet derived growth factor-R., insulin-R., insulin like growth factor-R., nerve growth factor amon others; glycolytic enzymes such as isoenzymes of enolase; phosphoglyceratemutase; lactate dehydrogenase (Nature 302, 218–223, 1983); vesicle proteins such as synatophysin; proteins with molecular weights of 30 kD, 94 kD and 105 kD (PNAS 85, 762–766, 1988); phosphorylated oncogenes such as v-fms (gp 140), pp 60 c-src, HER-2/new, polyoma virus middle T protein (56 kD) (Mol. Cell Biol. 8, 176–185, 1988) as well as further oncogene proteins which are derived from hormone receptors; cell skeleton proteins such as vinculin (Sci. Am. 246, 68–78, 1982) or calpactin (Mol. Cell. Biol. 6, 2745–2751, 1986); proteins in tumour cell lines, e.g. with molecular weights of: 150 kD, 130 kD, 110 kD, 170 kD, 100 kD, 80 kD, 210 kD, 70 kD, 60 kD (Int. J. Cancer 39, 482–487, 1987). Those proteins are preferably chosen for the determination in which the phosphotyrosine is stable since phosphatases present in serum can dephosphorylate phosphotyrosine in some proteins. Particularly suitable as stable, easily detectable proteins are synaptophysin, a N-glycosylated protein, which is bound firmly to the vesicle membrane and usually occurs in neurosecretory and neuroendocrine cells, chromogranin A, an acidic, soluble protein which occurs frequently in the granula of secretory cells and cytokeratins, intermediary filament proteins which are components of the cytoskeleton of epithelial cells. Therefore according to the present invention antibodies which are directed against these proteins are preferably used.

Depending on the method used, receptor $R_1$ is derivatized in such a way that it either mediates the binding to the solid phase if it is a heterogeneous immunoassay or it is derivatized in another way if it is a homogeneous immunoassay, for example by binding to latex particles or to modulator substances.

The determination according to the present invention is preferably carried out as a sandwich immunoassay. For this receptor $R_1$ is made immobilizable and reacted simultaneously or sequentially with the sample solution. Subsequently receptor $R_2$ is added. Complexes form from the immobilized receptor $R_1$, the substance to be detected as well as receptor $R_2$. Only complexes which are bound to the solid phase and which carry a label enter into the evaluation.

In this embodiment the receptor $R_1$ contains one of the two antibodies used according to the present invention or its derivative and mediates the binding to the solid phase. For this receptor $R_1$ can either be directly bound to a solid phase or via a spacer or it can even be immobilizable. In a preferred embodiment receptor $R_1$ is a conjugate of an antibody and a specifically bindable substance. The partner capable of binding to the specifically bindable substance is bound to a solid phase. Antigen-antibody; hapten-antibody; biotin-antibiotin-antibody; biotin-avidin; biotin-streptavidin; protein A-immuno-$\epsilon$-globulin can be cited as examples of specifically bindable pairs. In this embodiment a conjugate of the antibody with biotin is particularly preferably used as $R_1$ and a matrix is particularly preferably used as the solid phase which carries streptavidin on its surface. The immobilization of the monoclonal antibody then takes place by binding of the biotin to streptavidin. An embodiment is also preferred in which antibodies against the Fc part of the monoclonal antibodies used or protein A molecules are bound to the surface of the solid phase whereby the immobilization then takes place by binding of the Fc parts of the monoclonal antibodies.

In a further preferred embodiment biotin molecules are bound to a matrix and a conjugate of biotin and the antibody is used as receptor $R_1$. The immobilization can then take place after carrying out the immunological reaction by addition of streptavidin.

Materials which are usually used in immunological methods are suitable as the solid phase. For example polymer materials or also materials containing cellulose as well as glass can be used. Polystyrene, polymethacrylate, teflon, polyamide, copolymers of styrene and acrylonitrile, glass and cellulose products have proven to be particularly suitable. The matrix can be present in any form e.g. as tubes, microtitre plates, beads, film, powder, particles or fibre pad. Solid phases obtained according to one of the processes described in the Patent Application EP-A 0 269 092 are for example suitable.

In each case the receptor $R_2$ contains the other antibody or its derivative which is necessary according to the present invention. Moreover, receptor $R_2$ is constructed in such a way that it can contribute to the signal change. Receptor $R_2$ is labelled when used for a homogeneous or heterogeneous immunoassay which uses labelling. Radioactive substances, enzymes, fluorescent and chemiluminescent substances are suitable as the label. The detection of this labelling is carried out according to known methods. An enzyme is preferably used as the label. Enzmyes which are suitable are in particular peroxidase, alkaline phosphatase and $\beta$-galactosidase. The detection of the enzyme is carried out by addition of a substrate and measurement of the colour formed. In other variants of immunoassays receptor $R_2$ is bound to coated particles.

Receptor $R_2$ preferably contains an antibody capable of specifically binding to phosphorylated tyrosine as the antibody. An antibody capable of specifically binding to phosphorylated tyrosine can be obtained by immunizing a suitable organism with phosphotyramine in a known way, isolating the spleen cells which are fused with myeloma cells according to known methods and then the clones which are capable of binding to phosphotyrosine are selected and cultured. Phosphotyramine is bound to succinylated carrier proteins for the immunization in which keyhole limpet haemocyanin (KLH) and bovine serum albumin are preferably used as carrier proteins. The monoclonal antibody 3-365-10 produced by the cell line ECACC 90031904 is particularly preferably used.

In the incubation of the body fluid with the two receptors complexes form consisting of $R_1$, protein containing phosphorylated tyrosine and $R_2$. Only complexes in which all three components are bound can effect a change in signal. In this way, on the one hand, only a particular type of proteins and, on the other hand, only their phosphorus groups bound to tyrosine are specifically detected because only the corresponding proteins are capable of binding to the two specific antibodies. In the preferred embodiment of the sandwich immunoassay only complexes to which $R_1$ is bound can be immobilized and only complexes to which $R_2$ is in addition bound can be evaluated via the labelling.

The presence of particular proteins which contain two epitopes which are capable of binding to the two antibodies used can be detected with the method according to the present invention. Such fragments are mainly formed in tumour tissue.

The invention also provides a reagent for the detection of proteins containing phosphorylated tyrosine which is characterized in that it contains at least two receptors $R_1$ and $R_2$ in which one of the two receptors contains an antibody or its derivative capable of binding to the protein to be determined and the other receptor contains an antibody or its derivative capable of specifically binding to phosphorylated tyrosine.

The invention also provides the cell culture ECACC 90031904 deposited at the European Collection of Animal Cell Cultures, Port Down (GB) which produces antibodies which are capable of specifically binding to phosphorylated tyrosine.

The invention is elucidated by the following example.

EXAMPLE

Test Preparation With Synaptophysin as Antigen

Phosphorylated synaptophysin was detected in body fluids in a sandwich enzyme-immunoassay with an antibody which specifically catches synaptophysin and an antibody which specifically detects phosphotyrosine. Microtitre plates, coated with streptavidin analogous to EP-A 0 269 092, were coated for 2 h at room temperature with the synaptophysin-specific MAB SY 38 (2 μg/ml) produced by the cell line ECACC 89112801 as a biotin conjugate (produced by reacting the antibody with D-biotin-$\epsilon$-amino caproic acid-N-hydroxysuccinimide ester) in a volume of 100 nl PBS (8 g/l NaCl 0.2 g/l KCl 1.44 g/l $Na_2HPO_4 2H_2O$, 0.2 g/l $KH_2PO_4$) including 5 μl sample per well. After washing three times with 0.05% Tween 20/PBS it was then incubated with the conjugate of an antiphosphotyrosine antibody coupled to peroxidase (166 U/l incubation concentration) in PBS.

After incubating for 1 h at room temperature it was again washed three times with 0.05% Tween 20/PBS. After subsequent incubation (60 minutes) with the enzyme substrate ABTS (2,2'azino-di-[3-ethyl-benzthiazoline sulphonic acid (6)]-diammonium salt, 9.1 mmol/l ABTS, 1.47 mmol/l sodium perborate, 100 mmol/l phosphate-citrate buffer pH 5.0) at room temperature the absorbance was measured at 405 nm as a measure for the analyte concentration.

The test preparations with the catcher MAB anti-chromogranin (production analogous to Am. J. Surgical Pathology 8 (1984) 607–614) (2 μg/ml), with an anti-cytokeratin MAB with the deposit number ECACC 89030302 (3 μg/ml) as well as with an anti-calpactin MAB [produced according to Biochemistry 27 (1988) 2069–2076]were carried out analogously.

TABLE

Serum evaluation

| | SY 38 × Ptyr | | CA × PTyr | |
|---|---|---|---|---|
| | positive | examined | positive | examined |
| Healthy | 0 | 6 | 0 | 6 |
| Benign diseases | 0 | 10 | 0 | 10 |
| Malignant diseases | 9 | 50 | 9 | 50 |

| | CK × PTyr | | Calp. × PTyr | |
|---|---|---|---|---|
| | positive | examined | positive | examined |
| Healthy | 0 | 5 | 0 | 6 |
| Benign diseases | 0 | 13 | 0 | 10 |
| Malignant diseases | 4 | 19 | 2 | 12 |

PTyr = anti-phosphotyrosin MAB (ECACC 90031904)
SY 38 = anti-synaptophysin MAB (ECACC 89112801)
CA = anti-chromogranin MAB
CK = anti-cytokeratin MAB (ECACC 89030302)
Calp. = anti-calpactin MAB

We claim:

1. A method for the detection of proteins containing in vivo phosphorylated tyrosine in a sample of serum comprising the steps of:

incubating a sample of body fluid with at least two receptors $R_1$ and $R_2$, whereby at least two of said receptors bind to the substance to be detected and the binding of said receptors with the substance to be detected in the sample solution produces a detectable change in the sample solution, wherein one of the two receptors contains an antibody or its derivative capable of specifically binding to the protein to be detected, wherein said antibody cannot bind to phosphorylated tyrosine, and the other receptor contains an antibody or its derivative capable of specifically binding to phosphorylated tyrosine, and detecting the change in the sample solution produced by the binding of the receptors.

2. The method according to claim 1, wherein $R_1$ mediates binding to a solid phase and $R_2$ is a labeled receptor.

3. The method according to claim 2, further comprising separating the solid phase from a liquid phase and detecting the labeled receptor in one of the phases after separation.

4. The method according to claim 1, wherein phosphorylated tyrosine in synaptophysin, chromogranin A, calpactin or cytokeratins is detected and wherein receptor $R_1$ contains an antibody which is directed towards one of these proteins.

5. The method according to claim 1, wherein an antibody produced by the cell line ECACC 90031904 or its derivative is used as the antibody directed against phosphorylated tyrosine.

6. The method according to claim 2, wherein a matrix coated with streptavidin is used as the solid phase and receptor $R_1$ is a conjugate of biotin and an antibody or its derivative which specifically binds to the protein to be detected, whereby the binding of the antibody or its derivative to the solid phase takes place by means of the binding of biotin to streptavidin.

7. The method according to claim 1, wherein receptor $R_2$ is an antibody or its derivative which is capable of specifically binding to phosphorylated tyrosine and which is labelled with a fluorescent or chemiluminescent substance, radioactively or with an enzyme.

8. A reagent for the detection of proteins containing in vivo phosphorylated tyrosine in a body fluid, comprising at least two receptors $R_1$ and $R_2$ wherein one of the two receptors contains an antibody or its derivative which specifically binds to the protein to be determined, wherein said antibody cannot bind to phosphorylated tyrosine, and the other receptor contains an antibody or its derivative which specifically binds to phosphorylated tyrosine.

* * * * *